(12) United States Patent
Lin

(10) Patent No.: US 8,754,933 B2
(45) Date of Patent: Jun. 17, 2014

(54) MINIATURE PHOTOGRAPHIC APPARATUS

(75) Inventor: Wei-Teng Lin, Tainan (TW)

(73) Assignee: Medical Intubation Technology Corporation, Taoyuan Hsien (TW)

( * ) Notice: Subject to any disclaimer, the term of this patent is extended or adjusted under 35 U.S.C. 154(b) by 725 days.

(21) Appl. No.: 12/614,746

(22) Filed: Nov. 9, 2009

(65) Prior Publication Data

US 2010/0141745 A1    Jun. 10, 2010

(30) Foreign Application Priority Data

Dec. 5, 2008 (TW) ................................ 97147518 A

(51) Int. Cl.
*H04N 7/18* (2006.01)
*A61B 1/00* (2006.01)

(52) U.S. Cl.
CPC .................................. *A61B 1/00096* (2013.01)
USPC ..................................... 348/68; 348/E07.085

(58) Field of Classification Search
CPC ......................... A61B 1/00071; A61B 1/00096
USPC .............................................................. 348/68
See application file for complete search history.

(56) References Cited

U.S. PATENT DOCUMENTS

| | | | |
|---|---|---|---|
| 7,087,012 B2 * | 8/2006 | Ishibiki | 600/127 |
| 2003/0171653 A1 * | 9/2003 | Yokoi et al. | 600/160 |
| 2004/0267092 A1 * | 12/2004 | Ishibiki | 600/127 |
| 2005/0049462 A1 * | 3/2005 | Kanazawa | 600/170 |
| 2008/0117324 A1 * | 5/2008 | Minamio et al. | 348/340 |
| 2009/0225157 A1 * | 9/2009 | Orihara et al. | 348/76 |
| 2009/0225159 A1 * | 9/2009 | Schneider et al. | 348/82 |

* cited by examiner

*Primary Examiner* — Tung Vo
*Assistant Examiner* — Tyler Edwards
(74) *Attorney, Agent, or Firm* — Muncy, Geissler, Olds & Lowe, P.C.

(57) ABSTRACT

The present invention discloses a miniature photographic apparatus applicable to an endoscopic device, and including a casing, at least one light source device and at least one viewing lens device. The casing is disposed at a front end of the endoscopic device. The casing includes an accommodating space. The light source device is disposed in the accommodating space, and emits at least one light and includes a first protecting layer at a front end of the light source device. The viewing lens device is disposed in the accommodating space and includes a second protecting layer at a front end of the viewing lens device. The second protecting layer is separated from the first protecting layer to prevent lights reflected by the second protecting layer from entering into the viewing lens device.

14 Claims, 4 Drawing Sheets

MINIATURE PHOTOGRAPHIC APPARATUS

BACKGROUND OF THE INVENTION

1. Field of the Invention

The present invention relates to a miniature photographic apparatus, in particular to a miniature photographic apparatus of an endoscope having a protecting layer for separating a light source device and an imaging lens.

2. Description of the Related Art

At present, a conventional endoscopic device generally includes a slender flexible tube mainly composed of a photographic device and a light source. After the endoscopic device is connected with a display device, internal views such as a human organ, interior of a transportation means, components of an electronic device and cracks of a construction can be displayed on a screen, such that doctors, architects, electronic and mechanical engineers and technicians can diagnose a patient's illness, a human organ, or damages of a tool or a component by the image displayed on the screen. The endoscopic device can be used for inspections as long as there is a pore passage interconnected to the outside. For example, a digestive endoscope is inserted and passed through an oral cavity, or an intestinal endoscope is inserted and passed through an anus for examining esophagus, stomach and duodenum, and an endoscope is passed through a ventilation hole for inspecting a turbine blade. If there is no pore passage, the pore passage can be made by performing a surgical operation or removing a screw to achieve the aforementioned effects. For example, a laparoscopic examination requires making a hole at a patient's abdomen, and an arthroscope requires cutting open a patient's skin around a joint, and a casing is removed first for inspecting an engine.

Basically, an endoscopic examination is an intrusive examination, and an endoscopic device is entered or passed into a human body or an object. With reference to FIGS. 1 and 2 for an exploded view of a conventional endoscopic device and a top view of a conventional miniature photographic apparatus respectively, the endoscopic device 2 includes a light sensing element 21 and a miniature photographic apparatus, wherein the miniature photographic apparatus includes a light source device 27 and a viewing lens device 28, and the light source device 27 and the viewing lens device 28 are supported and fixed by a lens mount 23. The light sensing element 21 is installed on a connecting structure 24 and provided for generating a corresponding electronic signal according to an optical image, and transmitting the electronic signal to a processor 71, and then the processor 71 processes the electronic signal of the image and sends the electronic signals to a first display device 72, a second display device 73 or a third display device 74 to display the image.

Since the light source device 27 (such as an LED lamp) and the viewing lens device 28 share a same protecting layer 25, such that a portion of light 29 emitted from the light source device 27 travels to the protecting layer 25 and is reflected back into the viewing lens device 28 to cause the portion of image to be displayed in a reverse attribute, therefore the image cannot be displayed clearly.

Furthermore, a casing 26 at an end of the endoscopic device 2 has a front end in the form of a smooth flat circular body, and thus the light 29 of a light source device 27 will be interfered by the casing 26 and cannot travel normally, resulting in a lower uniformity of the image.

SUMMARY OF THE INVENTION

In view of the aforementioned shortcomings of the prior art, the inventor of the present invention provides a miniature photographic apparatus, wherein a light source device and an imaging lens have independent protecting layers, such that lights reflected from the protecting layer of the light source device will not enter into a viewing lens device.

Another objective of the present invention is to provide a miniature photographic apparatus having a plurality of recesses disposed at a front end of the casing of the light source device, such that lights emitted from the light source device can be passed through the plurality of recesses and travelled normally, so as to enhance the uniformity of the image substantially.

To achieve the foregoing objective, the present invention provides a miniature photographic apparatus applicable to an endoscopic device, and the miniature photographic apparatus comprises a casing, at least one light source device and at least one viewing lens device. The casing is disposed at a front end of the endoscopic device. The casing includes an accommodating space. At least one light source device is disposed in the accommodating space, and the light source device emits at least one light, and the light source device includes a first protecting layer at a front end of the light source device. At least one viewing lens device is disposed in the accommodating space and the viewing lens device includes a second protecting layer at a front end of the viewing lens device. The second protecting layer is separated from the first protecting layer to prevent lights reflected by the second protecting layer from entering into the viewing lens device.

The miniature photographic apparatus of the present invention can effectively process the operation and achieve the simplified function.

DETAILED DESCRIPTION OF THE PREFERRED EMBODIMENTS

The present invention will now be described in more detail hereinafter with reference to the accompanying drawings that show various embodiments of the invention as follows. Same numerals are used for same respective elements in the following embodiments.

Figure 1:
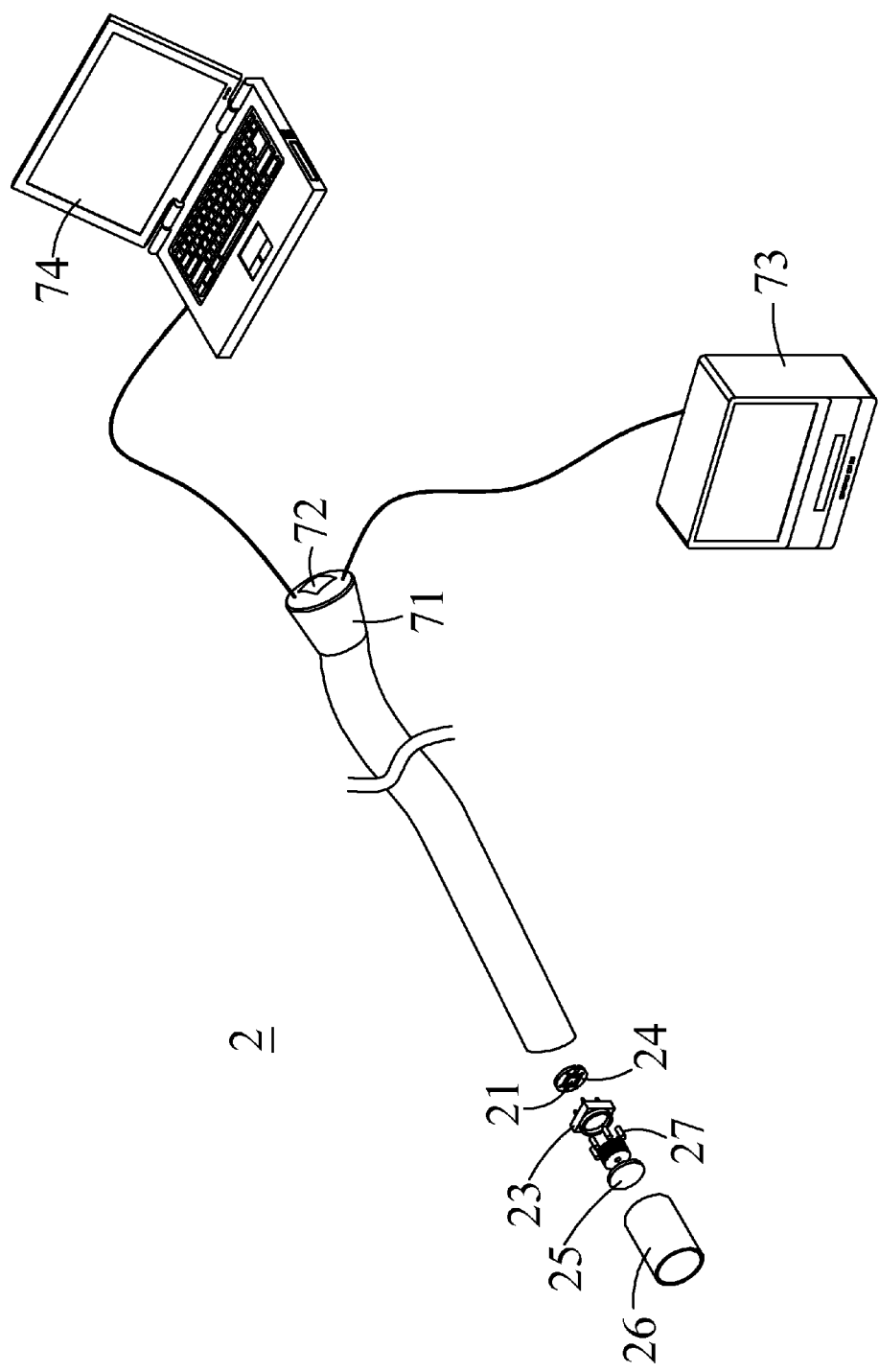
FIG. 1 is a perspective exploded view of a conventional endoscopic device.
Figure 2:
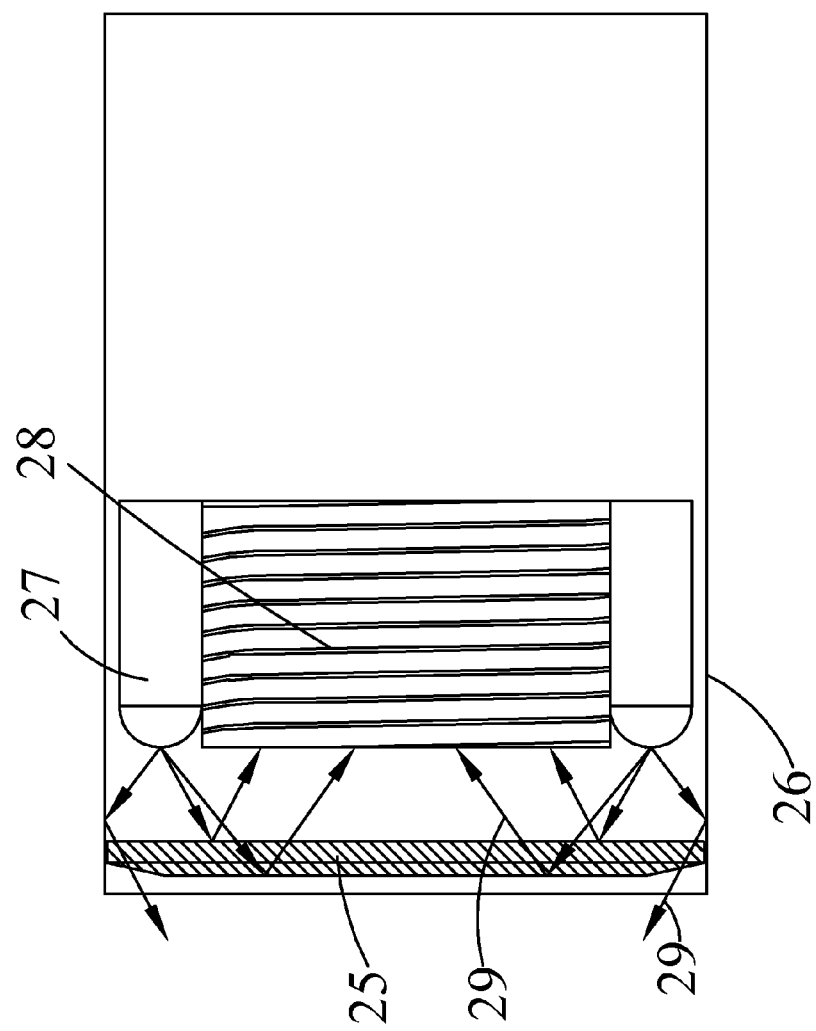
FIG. 2 is a top view of a conventional miniature photographic apparatus.
Figure 3:
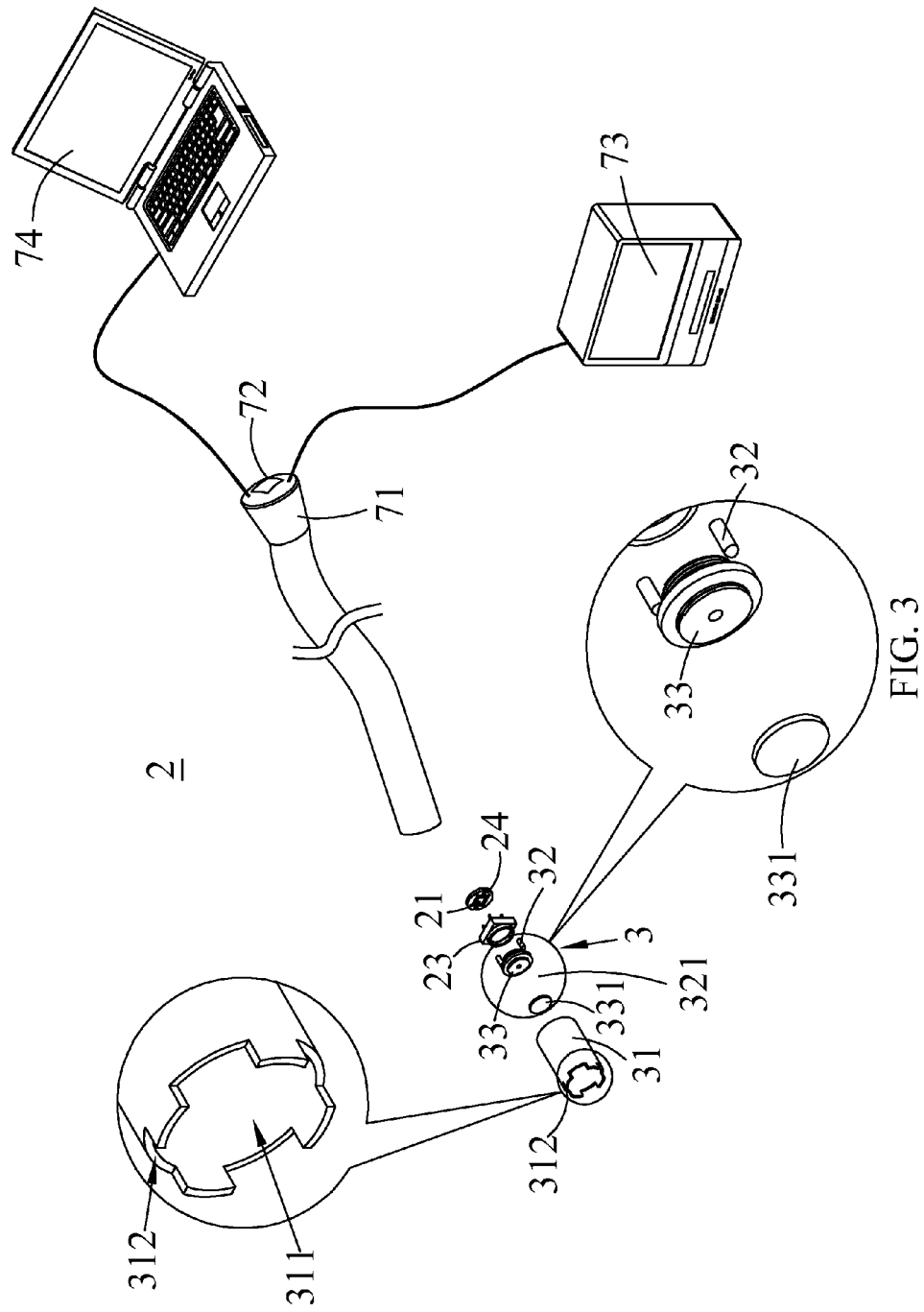
FIG. 3 is a perspective exploded view of a miniature photographic apparatus in accordance with the present invention.

With reference to FIG. 3 for a perspective exploded view of a miniature photographic apparatus in accordance with the present invention, the miniature photographic apparatus is applied to an endoscopic device. The endoscopic device 2 comprises a light sensing element 21 and a miniature photographic apparatus 3, wherein the miniature photographic apparatus 3 comprises a light source device 32 and a viewing lens device 33, wherein the light source device 32 is provided for emitting light to the outside, and the viewing lens device 33 is provided for collecting lights reflected from an external object to form an optical image, and the light source device 32 and the viewing lens device 33 are supported and fixed by a lens mount 23, as needed. The light sensing element 21 is installed on a connecting structure 24 for generating an electronic signal corresponding to the optical image and transmitting the electronic signal to a processor 71, and then the processor 71 processes the electronic signal of the image and provides the electronic signal to a first display device 72, a second display device 73 or a third display device 74 to display the image, so as to achieve the effects for electronic, industrial and medical inspections.

The endoscopic device 3 may be an euthyscope, an endoscope with a flexible and bendable viewing lens device, and a general slender flexible endoscope, and the light sensing element 21 may be a charge coupled device (CCD) or a complementary metal oxide semiconductor (CMOS) light emitting diode (LED) for converting an image into an electronic signal by optics.

Figure 4:
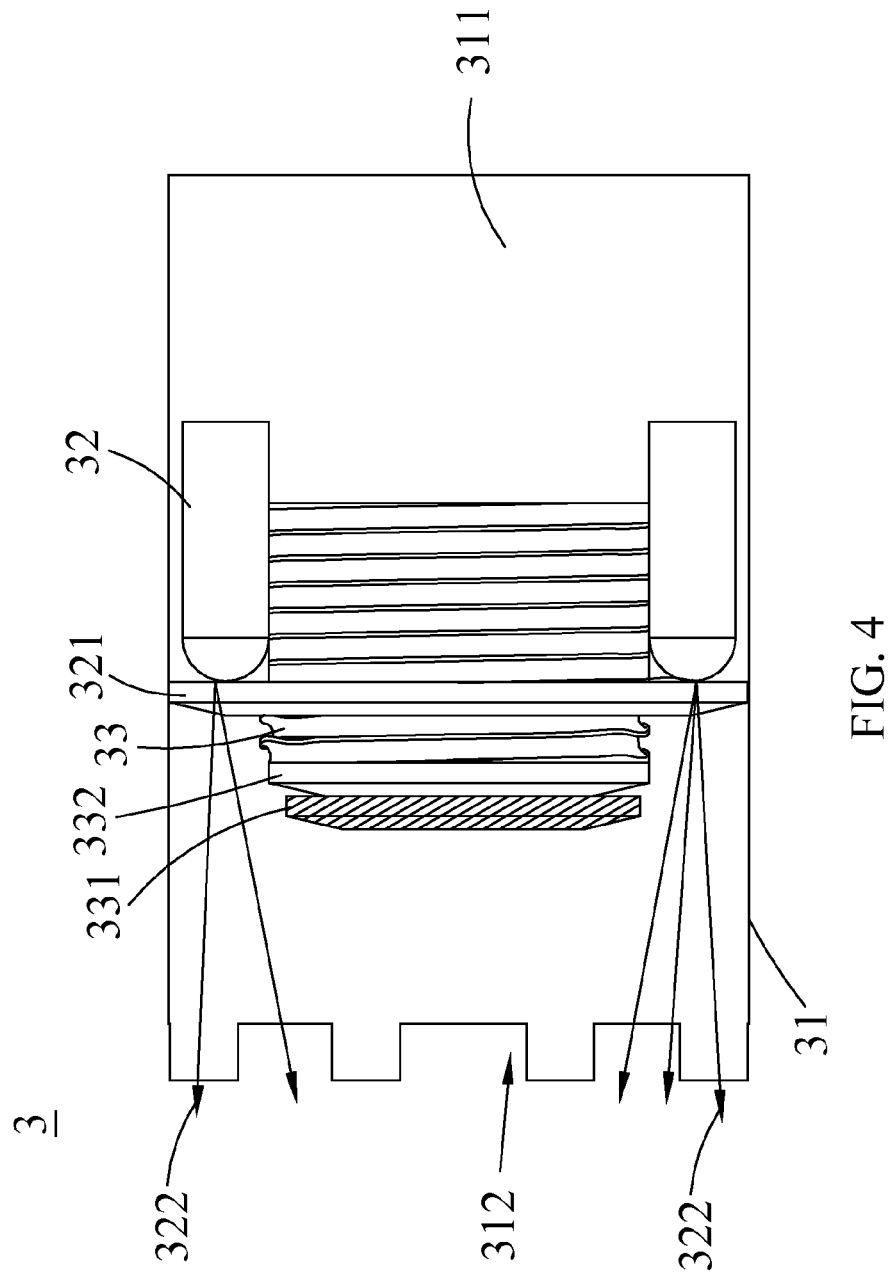
FIG. 4 is a schematic view of a miniature photographic apparatus in accordance with the present invention.

With reference to FIG. 4 for a top view of a miniature photographic apparatus in accordance with the present invention, the miniature photographic apparatus 3 is applied to an endoscopic device, and includes a miniature photographic apparatus comprising a casing 31, at least one light source device 32 and at least one viewing lens device 33. The casing 31 is disposed at a front end of the endoscopic device, and the casing 31 is hollow and includes an accommodating space 311 and a plurality of recesses 312, and the plurality of recesses 312 are disposed at the circumference of the front of the casing 31, and a portion of light 322 is emitted from the accommodating space 311 towards the recesses 312 to prevent the casing 31 from interfering the travelling of the portion of light 322. At least one light source device 32 is disposed in the accommodating space 311, and the light source device 32 includes a first protecting layer 321 at a front end of the light source device 32, and the first protecting layer 321 is a light transmitting transparent adhesive such as an ultraviolet (UV) adhesive or a light transmitting lens made of a glass, acrylic or plastic material for preventing the light source device from exposing directly to an external object or being damaged or corroded by a liquid, wherein the light source device 32 includes at least one light emitting diode (LED).

At least one viewing lens device 33 is disposed in the accommodating space 311, and the viewing lens device 33 includes a second protecting layer 331 and a hood structure 332 at a front end of the viewing lens device 33, wherein the second protecting layer 331 is a light transmitting lens made of a glass, acrylic or plastic material, or a light transmitting transparent adhesive such as an ultraviolet (UV) adhesive for preventing the viewing lens device 33 from exposing directly to an external object or being damaged or corroded by a liquid, and the hood structure 332 is disposed between the viewing lens device 33 and the second protecting layer 331 for isolating and preventing an external light from projecting into the viewing lens device 33 directly, such that the light 322 emitted from the light source device 32 is passed through the plurality of recesses 312 and travels at a wider light emitting angle. In addition, the casing 31 next to the recesses 312 can protect the viewing lens device 33 and prevent the casing 31 from being touched or collided or damages to the viewing lens device 33.

Since the second protecting layer 331 is separated from the first protecting layer 321, therefore the light 322 reflected from the second protecting layer 331 will not enter into the viewing lens device 33, and images displayed in reverse attribute can be reduced to provide a clearer captured image.

While the invention has been described by means of specific embodiments, numerous modifications and variations could be made thereto by those skilled in the art without departing from the scope and spirit of the invention set forth in the claims.

What is claimed is:

1. A miniature photographic apparatus applicable to an endoscopic device, said miniature photographic apparatus comprising:
   a casing disposed at a front end of said endoscopic device and defining an accommodating space;
   at least one light source device disposed in said accommodating space and arranged for emitting light, with a first protecting layer being a ring shape and disposed at a front end of said light source device; and
   at least one viewing lens device, having a columnar body, disposed in said accommodating space, with a second protecting layer disposed at a front end of said viewing lens device and said second protecting layer being separately formed from said first protecting layer and disposed without contacting said first protecting layer,
   wherein said first protecting layer is located between the casing and the viewing lens device and spaced from the front end of the viewing lens device,
   wherein the first protecting layer and the second protecting layer are independent from each other and spaced apart from each other, and
   wherein the first protecting layer is sleeved onto the columnar body of the at least one viewing lens device, the columnar body passing through the first protecting layer, the columnar body having a head end protruding out of the first protecting layer to be located in front of the first protecting layer.

2. The miniature photographic apparatus of claim 1, wherein said casing includes a plurality of recesses disposed at a front end thereof for emitting said light from said plurality of recesses.

3. The miniature photographic apparatus of claim 1, wherein a hood structure is disposed between said at least one viewing lens device and said second protecting layer for isolating external light from projecting directly into said at least one viewing lens device.

4. The miniature photographic apparatus of claim 1, wherein said first protecting layer is a light transmitting transparent adhesive for preventing said light source device from exposing directly to an external object or being damaged or corroded by a liquid.

5. The miniature photographic apparatus of claim 4, wherein said light transmitting transparent adhesive is an ultraviolet (UV) adhesive.

6. The miniature photographic apparatus of claim 1, wherein said first protecting layer is a light transmitting lens for preventing said light source device from exposing directly to an external object or being damaged or corroded by a liquid.

7. The miniature photographic apparatus of claim 6, wherein said light transmitting lens is made of a glass, acrylic or plastic material.

8. The miniature photographic apparatus of claim 1, wherein said second protecting layer is a light transmitting transparent adhesive for preventing said viewing lens device from exposing directly to an external object or being damaged or corroded by a liquid.

9. The miniature photographic apparatus of claim 8, wherein said light transmitting transparent adhesive is an ultraviolet (UV) adhesive.

10. The miniature photographic apparatus of claim 1, wherein said second protecting layer is a light transmitting lens for preventing said viewing lens device from exposing directly an external object or being damaged or corroded by a liquid.

11. The miniature photographic apparatus of claim 10, wherein said light transmitting lens is made of a glass, acrylic or plastic material.

12. The miniature photographic apparatus of claim 1, wherein said light source device comprises a light emitting diode (LED).

13. The miniature photographic apparatus of claim 1, wherein said first protecting layer is parallel to said second protecting layer and disposed between said second protecting layer and the at least one light source device.

14. The miniature photographic apparatus of claim 1, wherein the first protecting layer is coaxial with the columnar body of the viewing lens device.

* * * * *